United States Patent
Ioffe et al.

(10) Patent No.: US 9,284,276 B2
(45) Date of Patent: Mar. 15, 2016

(54) N-ETHYL-N-PHENYL-1,2-DIHYDRO-4,5-DI-HYDROXY-1-METHYL-2-OXO-3-QUINOLINECARBOXAMIDE, PREPARATION AND USES THEREOF

(71) Applicants: Vladimir Ioffe, Kfar Saba (IL); Konstantin Ulanenko, Natania (IL); Avital Laxer, Tel-Aviv (IL); Muhammad Safadi, Nazareth (IL); Danit Licht, Givat Shmuel (IL); Ioana Lovinger, Kfar Saba (IL); Ulf Tomas Fristedt, Helsingborg (SE)

(72) Inventors: Vladimir Ioffe, Kfar Saba (IL); Konstantin Ulanenko, Natania (IL); Avital Laxer, Tel-Aviv (IL); Muhammad Safadi, Nazareth (IL); Danit Licht, Givat Shmuel (IL); Ioana Lovinger, Kfar Saba (IL); Ulf Tomas Fristedt, Helsingborg (SE)

(73) Assignee: TEVA PHARMACEUTICAL INDUSTRIES, LTD., Petach-Tikva (IL)

( * ) Notice: Subject to any disclaimer, the term of this patent is extended or adjusted under 35 U.S.C. 154(b) by 0 days.

(21) Appl. No.: 13/768,919

(22) Filed: Feb. 15, 2013

(65) Prior Publication Data
US 2013/0217724 A1  Aug. 22, 2013

Related U.S. Application Data

(60) Provisional application No. 61/599,680, filed on Feb. 16, 2012.

(51) Int. Cl.
| C07D 215/56 | (2006.01) |
| A61K 31/4704 | (2006.01) |
| A61J 1/03 | (2006.01) |

(52) U.S. Cl.
CPC .............. *C07D 215/56* (2013.01); *A61J 1/035* (2013.01); *A61K 31/4704* (2013.01)

(58) Field of Classification Search
None
See application file for complete search history.

(56) References Cited

U.S. PATENT DOCUMENTS

| 4,547,511 A | 10/1985 | Eriksoo et al. |
| 4,782,155 A | 11/1988 | Nakagawa et al. |
| 5,139,878 A | 8/1992 | Kim et al. |
| 6,077,851 A | 6/2000 | Bjork et al. |
| 6,121,287 A | 9/2000 | Bjork et al. |
| 6,133,285 A | 10/2000 | Bjork et al. |
| 6,589,616 B2 * | 7/2003 | Muggli et al. ............... 428/35.2 |
| 6,593,343 B2 | 7/2003 | Bjork et al. |
| 6,605,616 B1 | 8/2003 | Bjork et al. |
| 6,875,869 B2 | 4/2005 | Jansson |
| 7,514,068 B2 | 4/2009 | Tung et al. |
| 7,528,131 B2 | 5/2009 | Persichetti et al. |
| 7,560,557 B2 | 7/2009 | Jansson |
| 7,589,208 B2 | 9/2009 | Jansson |
| 7,884,208 B2 | 2/2011 | Frenkel et al. |
| 7,989,473 B2 | 8/2011 | Patashnik et al. |
| 8,178,127 B2 | 5/2012 | Safadi et al. |
| 8,252,933 B2 | 8/2012 | Gant et al. |
| 8,383,645 B2 | 2/2013 | Patashnik et al. |
| 2002/0173520 A1 | 11/2002 | Bjork et al. |
| 2005/0192315 A1 | 9/2005 | Jansson et al. |
| 2005/0215586 A1 | 9/2005 | Jansson et al. |
| 2009/0162432 A1 * | 6/2009 | Safadi et al. .................. 424/465 |
| 2009/0232889 A1 | 9/2009 | Jansson et al. |
| 2010/0209506 A1 | 8/2010 | Eisenreich |
| 2010/0266990 A1 * | 10/2010 | Cooley et al. .............. 433/228.1 |
| 2010/0322900 A1 | 12/2010 | Tarcic et al. |
| 2011/0027219 A1 | 2/2011 | Tarcic et al. |
| 2011/0034508 A1 | 2/2011 | Hayardeny et al. |
| 2011/0112141 A1 | 5/2011 | Frenkel et al. |
| 2011/0118308 A1 | 5/2011 | Frenkel et al. |
| 2011/0217295 A1 | 9/2011 | Haviv et al. |
| 2011/0218179 A1 | 9/2011 | Haviv et al. |
| 2011/0218203 A1 | 9/2011 | Kaye et al. |
| 2011/0251235 A1 | 10/2011 | Patashnik et al. |
| 2012/0010238 A1 | 1/2012 | Piryatinsky |
| 2012/0010239 A1 | 1/2012 | Fristedt |
| 2012/0142730 A1 | 6/2012 | Tarcic et al. |
| 2012/0225124 A1 | 9/2012 | Safadi et al. |
| 2013/0028866 A1 | 1/2013 | Gilgun et al. |
| 2013/0029916 A1 | 1/2013 | Gilgun et al. |
| 2013/0096158 A1 | 4/2013 | Hallak et al. |
| 2013/0203807 A1 | 8/2013 | Tarcic et al. |
| 2013/0259856 A1 | 10/2013 | Kaye |
| 2013/0272996 A1 | 10/2013 | Tarcic at al. |
| 2013/0303569 A1 | 11/2013 | Bar-Zohar |
| 2013/0345256 A1 | 12/2013 | Laxer et al. |
| 2013/0345257 A1 | 12/2013 | Hahn et al. |
| 2014/0017226 A1 | 1/2014 | Bar-Zohar et al. |
| 2014/0045886 A1 | 2/2014 | Martino et al. |
| 2014/0045887 A1 | 2/2014 | Martino at al. |

(Continued)

FOREIGN PATENT DOCUMENTS

| EP | 1073639 | 11/2002 |
| EP | 1097139 | 12/2002 |

(Continued)

OTHER PUBLICATIONS

PCT International Search Report issued Apr. 24, 2013 in connection with PCT International Application No. PCT/US13/26476.

(Continued)

*Primary Examiner* — David J Blanchard
*Assistant Examiner* — Sarah Chickos
(74) *Attorney, Agent, or Firm* — John P. White; Gary J. Gershik; Cooper & Dunham LLP

(57) ABSTRACT

The subject invention provides a pharmaceutical composition containing laquinimod or a pharmaceutically acceptable salt thereof, and a compound of N-ethyl-N-phenyl-1,2-dihydro-4,5-di-hydroxy-1-methyl-2-oxo-3-quinolinecarboxamide or a salt thereof.

17 Claims, No Drawings

(56) References Cited

U.S. PATENT DOCUMENTS

| | | |
|---|---|---|
| 2014/0105850 A1 | 4/2014 | Tarcic et al. |
| 2014/0107154 A1 | 4/2014 | Filippi et al. |
| 2014/0128430 A1 | 5/2014 | Frenkel et al. |

FOREIGN PATENT DOCUMENTS

| | | |
|---|---|---|
| EP | 1095021 | 9/2003 |
| EP | 1511732 | 12/2006 |
| EP | 1720531 | 4/2011 |
| WO | WO 90/15052 | 12/1990 |
| WO | WO 99/55678 | 11/1999 |
| WO | WO 00/03991 | 1/2000 |
| WO | WO 00/03992 | 1/2000 |
| WO | WO 00/74654 | 12/2000 |
| WO | WO 03/106424 | 12/2003 |
| WO | WO 2005/074899 | 8/2005 |

OTHER PUBLICATIONS

Written Opinion of the International Searching Authority issued Apr. 24, 2013 in connection with PCT International Application No. PCT/US13/26476.

PCT International Search Report issued Nov. 21, 2011 in connection with PCT International Application No. PCT/US11/43383.

Written Opinion of the International Searching Authority issued Nov. 21, 2011 in connection with PCT International Application No. PCT/US11/43383.

PCT International Search Report issued Nov. 29, 2011 in connection with PCT International Application No. PCT/US11/43391.

Written Opinion of the International Searching Authority issued Nov. 29, 2011 in connection with PCT International Application No. PCT/US11/43391.

PCT International Preliminary Report on Patentability issued Mar. 8, 2011 in connection with PCT International Application No. PCT/US2009/055692.

PCT International Search Report issued Apr. 21, 2010 in connection with PCT International Application No. PCT/US2009/055692.

Written Opinion of the International Searching Authority issued Apr. 21, 2010 in connection with PCT International Application No. PCT/US2009/055692.

International Preliminary Report on Patentability issued Jan. 15, 2013 in connection with PCT International Application No. PCT/US2011/043391.

International Preliminary Report on Patentability issued Jan. 15, 2013 in connection with PCT International Application No. PCT/US2011/043383.

European Search Report completed Aug. 10, 2011 in connection with European Patent Application No. EP 9812145.2.

Oct. 30, 2012 Office Action issued in connection with Chinese Patent Application No. 200980135007.1 (including English language translation).

Mar. 12, 2013 Response to Oct. 30, 2012 Office Action filed in connection with Chinese Patent Application No. 200980135007.1.

Notice of Allowance issued by the U.S. Patent and Trademark Office on Apr. 27, 2012 in connection with U.S. Appl. No. 12/552,663.

Office Action issued by the U.S. Patent and Trademark Office on Jan. 12, 2012 in connection with U.S. Appl. No. 12/552,663.

Apr. 12, 2012 Amendment in Response to Jan. 12, 2012 Office Action filed with the U.S. Patent and Trademark Office in connection with U.S. Appl. No. 12/552,663.

Office Action issued by the U.S. Patent and Trademark Office on Feb. 13, 2013 in connection with U.S. Appl. No. 13/178,842.

Mar. 25, 2013 Office Action issued by the U.S. Patent and Trademark Office in connection with U.S. Appl. No. 13/178,865.

Jönsson, Stig et al. (2004) "Synthesis and Biological Evaluation of New 1,2-Dihydro-4-hydroxy-2-oxo-3-guinolinecar boxamides . . . " J. of Medicinal Chemistry, 4:2075-88.

Wennerbert et al. (2007) "Development of a Practical and Reliable Synthesis of Laquinimod", Organic Process Research & Development. 111:674-680.

Tuvesson et al. (2005) "Cytochrome P450 3A4 is the Major Enzyme Responsible for the Metabolism of Laquinimod . . . " Drug Metabolism and Disposition. 33(6):866-872.

Nov. 4, 2014 Supplementary European Search Report issued by the European Patent Office in connection with European Patent Application No. EP 13749429.0, regional stage of PCT International Application No. PCT/US2013/026476, filed Feb. 15, 2013.

\* cited by examiner

N-ETHYL-N-PHENYL-1,2-DIHYDRO-4,5-DI-HYDROXY-1-METHYL-2-OXO-3-QUINOLINECARBOXAMIDE, PREPARATION AND USES THEREOF

This application claims benefit of U.S. Provisional Application No. 61/599,680, filed Feb. 16, 2012, the entire content of which is hereby incorporated by reference herein.

Throughout this application various publications, published patent applications, and patents are referenced. The disclosures of these documents in their entireties are hereby incorporated by reference into this application in order to more fully describe the state of the art to which this invention pertains.

BACKGROUND OF THE INVENTION

Laquinimod is a compound which has been shown to be effective in the acute experimental autoimmune encephalomyelitis (aEAE) model (U.S. Pat. No. 6,077,851). Its chemical name is N-ethyl-N-phenyl-1,2-dihydro-4-hydroxy-5-chloro-1-methyl-2-oxoquinoline-3-carboxamide, and its Chemical Registry number is 248281-84-7. The processes of synthesis of laquinimod and the preparation of its sodium salt are disclosed in U.S. Pat. No. 6,077,851. An additional process of synthesis of laquinimod is disclosed in U.S. Pat. No. 6,875,869. Pharmaceutical compositions comprising laquinimod sodium are disclosed in PCT International Application Publication No. WO 2005/074899.

Laquinimod sodium has high oral bioavailability and has been suggested as an oral formulation for the treatment of Multiple Sclerosis (MS). (Polman, C. et al., (2005) "Treatment with laquinimod reduces development of active MRI lesions in relapsing MS", Neurology. 64:987-991; Sandberg-Wollheim M, et al. (2005) "48-week open safety study with high-dose oral laquinimod in patients", *Mult Scler.* 11:S154). Studies have also shown that laquinimod can reduce development of active MRI lesions in relapsing MS. (Polman, C. et al., (2005) "Treatment with laquinimod reduces development of active MRI lesions in relapsing MS", Neurology. 64:987-991).

SUMMARY OF THE INVENTION

The subject invention provides an isolated compound having the structure:

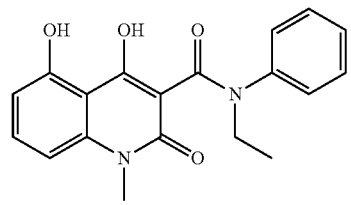 [SMILES: CCN(C(=O)c1c(O)c2c(O)cccc2n(C)c1=O)c1ccccc1]

or a salt thereof.

The subject invention also provides a composition comprising a compound having the structure:

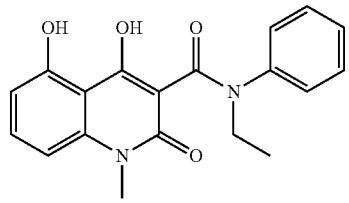 [SMILES: CCN(C(=O)c1c(O)c2c(O)cccc2n(C)c1=O)c1ccccc1]

or a salt thereof,
wherein the composition is free of laquinimod or a salt thereof.

The subject invention further provides a process for preparing N-ethyl-N-phenyl-1,2-dihydro-4,5-di-hydroxy-1-methyl-2-oxo-3-quinolinecarboxamide comprising reacting a compound having the structure:

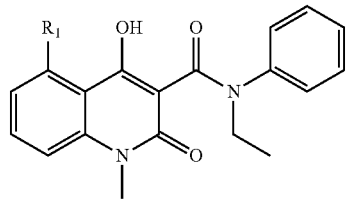

wherein $R_1$ is methyl, ethyl, halogen, MeO—, EtO—, —$CF_3$, pF-PhO—, MeS—, —$NO_2$, or —$N(CH_3)_2$,
with an oxidizing agent when $R_1$ is methyl, ethyl or —$CF_3$;
with a base when $R_1$ is halogen; or
with a Lewis acid when $R_1$ is MeO—, EtO— or pF-PhO—, MeS—, —$NO_2$, or —$N(CH_3)_2$.

The subject invention yet further provides a process for purifying N-ethyl-N-phenyl-1,2-dihydro-4,5-di-hydroxy-1-methyl-2-oxo-3-quinolinecarboxamide comprising the steps of:
 a) reacting N-ethyl-N-phenyl-1,2-dihydro-4,5-di-hydroxy-1-methyl-2-oxo-3-quinolinecarboxamide with an anhydride in a first solvent;
 b) removing the first solvent from the reaction mixture of step a) to obtain an residual oil;
 c) dissolving the residual oil in a second solvent;
 d) adding a basic solution to the solution from step c);
 e) obtaining the purified N-ethyl-N-phenyl-1,2-dihydro-4,5-di-hydroxy-1-methyl-2-oxo-3-quinolinecarboxamide from reaction mixture of step d).

The subject invention yet further provides a pharmaceutical composition comprising laquinimod or a pharmaceutically acceptable salt thereof, and N-ethyl-N-phenyl-1,2-dihydro-4,5-di-hydroxy-1-methyl-2-oxo-3-quinolinecarboxamide or a salt thereof, wherein N-ethyl-N-phenyl-1,2-dihydro-4,5-di-hydroxy-1-methyl-2-oxo-3-quinolinecarboxamide is present in the composition in an amount greater than about 0.02% and less than about 0.50%, by weight, relative to the amount of laquinimod, based on a determination by an HPLC method.

The subject invention yet further provides a pharmaceutical composition comprising laquinimod or a pharmaceutically acceptable salt thereof, at least one pharmaceutically acceptable carrier, and a light-resistant coating wherein the coating is resistant to light with wavelength in the range of 310-400 nm.

The subject invention yet further provides a process for preparing a pharmaceutical composition comprising laquinimod or a pharmaceutically acceptable salt thereof, comprising: admixing laquinimod or a pharmaceutically acceptable salt thereof with at least one pharmaceutically acceptable carrier in a low-light environment to form the pharmaceutical composition.

The subject invention yet further provides a process for preparing a validated pharmaceutical composition comprising laquinimod or a pharmaceutically acceptable salt thereof, and at least one pharmaceutically acceptable carrier, comprising:
  a) obtaining a batch of laquinimod or a pharmaceutically acceptable salt thereof;
  b) determining the amount of N-ethyl-N-phenyl-1,2-dihydro-4,5-di-hydroxy-1-methyl-2-oxo-3-quinolinecarboxamide in the batch using a suitable apparatus; and
  c) preparing the pharmaceutical composition from the batch only if the batch is determined to have less than about 0.50% N-ethyl-N-phenyl-1,2-dihydro-4,5-di-hydroxy-1-methyl-2-oxo-3-quinolinecarboxamide by weight relative to the amount of laquinimod.

The subject invention yet further provides a process for preparing a packaged pharmaceutical composition comprising laquinimod sodium comprising:
  a) obtaining a pharmaceutical composition of laquinimod or a pharmaceutically acceptable salt thereof;
  b) analyzing the pharmaceutical composition for the presence of N-ethyl-N-phenyl-1,2-dihydro-4,5-di-hydroxy-1-methyl-2-oxo-3-quinolinecarboxamide; and
  c) packaging the pharmaceutical composition in a light-resistant packaging only if the content of N-ethyl-N-phenyl-1,2-dihydro-4,5-di-hydroxy-1-methyl-2-oxo-3-quinolinecarboxamide is less than about 0.50% by weight relative to the amount of laquinimod.

The subject invention yet further provides a process of distributing a validated batch of a pharmaceutical composition comprising laquinimod or a pharmaceutically acceptable salt thereof and at least one pharmaceutically acceptable carrier, comprising:
  a) obtaining a batch of the pharmaceutical composition;
  b) performing stability testing with a sample of the batch;
  c) determining the total amount of N-ethyl-N-phenyl-1,2-dihydro-4,5-di-hydroxy-1-methyl-2-oxo-3-quinolinecarboxamide in the sample of the batch by a suitable apparatus after stability testing;
  d) validating the batch for distribution only if the sample of the batch after stability testing is determined to have less than about 0.50% by weight of N-ethyl-N-phenyl-1,2-dihydro-4,5-di-hydroxy-1-methyl-2-oxo-3-quinolinecarboxamide relative to the amount of laquinimod; and
  e) distributing the validated batch.

The subject invention yet further provides N-ethyl-N-phenyl-1,2-dihydro-4,5-di-hydroxy-1-methyl-2-oxo-3-quinolinecarboxamide or a salt thereof for use, as a reference standard to detect trace amounts of N-ethyl-N-phenyl-1,2-dihydro-4,5-di-hydroxy-1-methyl-2-oxo-3-quinolinecarboxamide in a pharmaceutical composition comprising laquinimod or a pharmaceutically acceptable salt of laquinimod.

The subject invention yet further provides a method for treating Multiple Sclerosis in a patient comprising administering to the patient an amount of the pharmaceutical composition described herein effective to treat Multiple Sclerosis in the patient.

The subject invention yet further provides a sealed package containing a pharmaceutical composition comprising laquinimod or a pharmaceutically acceptable salt thereof and at least one pharmaceutically acceptable carrier, wherein the sealed package is light resistant packaging.

DETAILED DESCRIPTION OF THE INVENTION

Laquinimod is a small molecule having the following chemical structure:

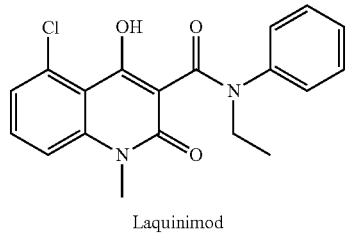 [SMILES: CCN(C(=O)c1c(O)c2c(Cl)cccc2n(C)c1=O)c1ccccc1]

Laquinimod

It is an oral immunomodulator which has demonstrated therapeutic effect in various experimental inflammatory/autoimmune animal models, such as Experimental Autoimmune Encephalomyelitis (EAE), an animal model for Multiple Sclerosis (MS), Dextran Sodium Sulphate (DSS) induced colitis for Inflammatory Bowel Disease, Non-Obese Diabetic (NOD) mice for Type I Diabetes (IDDM), Experimental Autoimmune Neuritis (EAN) for Guillain-Barre Syndrome, Systemic Lupus Erythematosus (SLE), lupus nephritis, lupus arthritis, Crohn's Disease and Rheumatoid arthritis. The therapeutic activity of laquinimod in these models results from a variety of mechanistic effects, including reduction of leukocyte infiltration into target tissues by modulation of chemokine-mediated T-cell adhesion, modulation of cytokine balance, down regulation of MHC class II resulting in alteration of antigen presentation, and effects on dendritic cells subpopulations.

A pharmaceutically acceptable salt of laquinimod includes lithium, sodium, potassium, magnesium, calcium, manganese, copper, zinc, aluminum and iron. Salt formulations of laquinimod and the process for preparing the same are described, e.g., in U.S. Patent Application Publication No. 2005/0192315 and PCT International Application Publication No. WO 2005/074899, which are hereby incorporated by reference into this application.

It has been found that when laquinimod or a salt thereof is exposed to light under certain conditions, an impurity can form. This impurity was identified to be N-Ethyl-N-phenyl-1,2-dihydro-4,5-di-hydroxy-1-methyl-2-oxo-3-quinolinecarboxamide ("5-HLAQ"), having the following structure:

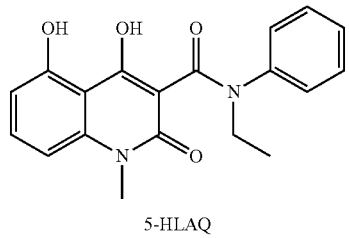 [SMILES: CCN(C(=O)c1c(O)c2c(O)cccc2n(C)c1=O)c1ccccc1]

5-HLAQ

Not to be bound by a particular theory, this impurity is suspected to be formed via a substitution reaction in which a chlorine group is substituted for a hydroxyl group.

The subject invention provides an isolated compound having the structure:

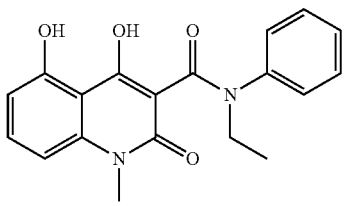 [SMILES: CCN(C(=O)c1c(O)c2c(O)cccc2n(C)c1=O)c1ccccc1]

or a salt thereof.

The subject invention also provides a composition comprising a compound having the structure:

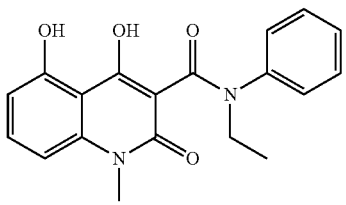 [SMILES: CCN(C(=O)c1c(O)c2c(O)cccc2n(C)c1=O)c1ccccc1]

or a salt thereof,
wherein the composition is free of laquinimod or a salt thereof.

The subject invention further provides a process for preparing N-ethyl-N-phenyl-1,2-dihydro-4,5-di-hydroxy-1-methyl-2-oxo-3-quinolinecarboxamide comprising reacting a compound having the structure:

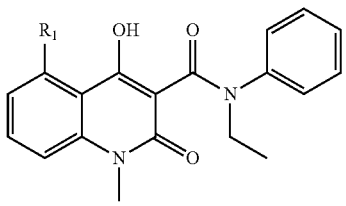

wherein $R_1$ is methyl, ethyl, halogen, MeO—, EtO—, —CF$_3$, pF-PhO—, MeS—, —NO$_2$, or —N(CH$_3$)$_2$,
with an oxidizing agent when $R_1$ is methyl, ethyl or —CF$_3$;
with a base when $R_1$ is halogen; or
with a Lewis acid when $R_1$ is MeO—, EtO— or pF-PhO—, MeS—, —NO$_2$, or —N(CH$_3$)$_2$.

In an embodiment of the process, $R_1$ is MeO—.

In another embodiment of the process, the Lewis acid is AlCl$_3$.

In yet another embodiment of the process, the solvent is an anhydrous solvent.

The subject invention yet further provides a process for purifying N-ethyl-N-phenyl-1,2-dihydro-4,5-di-hydroxy-1-methyl-2-oxo-3-quinolinecarboxamide comprising the steps of:
a) reacting N-ethyl-N-phenyl-1,2-dihydro-4,5-di-hydroxy-1-methyl-2-oxo-3-quinolinecarboxamide with an anhydride in a first solvent;
b) removing the first solvent from the reaction mixture of step a) to obtain an residual oil;
c) dissolving the residual oil in a second solvent;
d) adding a basic solution to the solution from step c);
e) obtaining the purified N-ethyl-N-phenyl-1,2-dihydro-4,5-di-hydroxy-1-methyl-2-oxo-3-quinolinecarboxamide from reaction mixture of step d).

In an embodiment of the process the anhydride is acetic anhydride.

In another embodiment of the process, the first solvent is acetic anhydride.

In yet another embodiment of the process, the second solvent is dichloromethane.

In yet another embodiment of the process, the basic solution is NaOH solution.

The subject invention yet further provides a pharmaceutical composition comprising laquinimod or a pharmaceutically acceptable salt thereof, and N-ethyl-N-phenyl-1,2-dihydro-4,5-di-hydroxy-1-methyl-2-oxo-3-quinolinecarboxamide or a salt thereof, wherein N-ethyl-N-phenyl-1,2-dihydro-4,5-di-hydroxy-1-methyl-2-oxo-3-quinolinecarboxamide is present in the composition in an amount greater than about 0.02% and less than about 0.50%, by weight, relative to the amount of laquinimod, based on a determination by an HPLC method.

In an embodiment of the pharmaceutical composition, the amount of N-ethyl-N-phenyl-1,2-dihydro-4,5-di-hydroxy-1-methyl-2-oxo-3-quinolinecarboxamide in the composition is less than about 0.10% by weight relative to the amount of laquinimod.

In another embodiment of the pharmaceutical composition, the total amount of N-ethyl-N-phenyl-1,2-dihydro-4,5-di-hydroxy-1-methyl-2-oxo-3-quinolinecarboxamide is greater than about 0.05% by weight relative to the amount of laquinimod.

In yet another embodiment of the pharmaceutical composition, the pharmaceutical composition comprises the pharmaceutically acceptable salt of laquinimod which is a sodium salt.

In yet another embodiment of the pharmaceutical composition, the pharmaceutical composition comprises at least one pharmaceutically acceptable carrier.

In yet another embodiment of the pharmaceutical composition, the at least one pharmaceutically acceptable carrier is magnesium stearate.

In yet another embodiment of the pharmaceutical composition, the pharmaceutical composition is in the form of a capsule.

In yet another embodiment of the pharmaceutical composition, the pharmaceutical composition is in the form of a tablet.

In yet another embodiment of the pharmaceutical composition, the tablet is coated with a light-resistant coating.

In yet another embodiment of the pharmaceutical composition, the light-resistant coating is a coating comprising titanium dioxide.

The subject invention yet further provides a pharmaceutical composition comprising laquinimod or a pharmaceutically acceptable salt thereof, at least one pharmaceutically acceptable carrier, and a light-resistant coating wherein the coating is resistant to light with wavelength in the range of 310-400 nm.

In an embodiment of the pharmaceutical composition, the light-resistant coating is a coating comprising titanium dioxide.

In another embodiment of the pharmaceutical composition, the pharmaceutical composition is in a solid form tablet.

In another embodiment of the pharmaceutical composition, the pharmaceutical composition is in the form of a tablet.

In another embodiment of the pharmaceutical composition, the pharmaceutical composition is in the form of a capsule.

In another embodiment, the pharmaceutical composition is in light-resistant packaging. In another embodiment the light-resistant packaging is an opaque blister pack or an opaque high density polyethylene (HPDE) container.

The subject invention yet further provides a process for preparing a pharmaceutical composition comprising laquinimod or a pharmaceutically acceptable salt thereof, comprising: admixing laquinimod or a pharmaceutically acceptable salt thereof with at least one pharmaceutically acceptable carrier in a low-light environment to form the pharmaceutical composition.

In an embodiment of the process, the pharmaceutical composition further comprises N-ethyl-N-phenyl-1,2-dihydro-4,5-di-hydroxy-1-methyl-2-oxo-3-quinolinecarboxamide in an amount of less than 0.5% by weight relative to the amount of laquinimod.

In an embodiment of the process, the laquinimod or the pharmaceutically acceptable salt thereof is admixed with a liquid to form a solution.

In another embodiment of the process, the liquid is water.

In yet another embodiment of the process, the solution is combined with at least one solid pharmaceutical excipient to form a wet granulate.

In yet another embodiment of the process, the process further comprises drying the wet granulate in a low-light environment.

In yet another embodiment of the process, the process further comprises compressing the dried granulate into tablets in a low-light environment.

In yet another embodiment of the process, the process further comprises filling the dried granulate into capsules in a low-light environment.

In yet another embodiment of the process, the low-light environment is an environment within non-transparent vessels or an environment in which only yellow fluorescent light present.

The subject invention yet further provides a process for preparing a validated pharmaceutical composition comprising laquinimod or a pharmaceutically acceptable salt thereof, and at least one pharmaceutically acceptable carrier, comprising:
    a) obtaining a batch of laquinimod or a pharmaceutically acceptable salt thereof;
    b) determining the amount of N-ethyl-N-phenyl-1,2-dihydro-4,5-di-hydroxy-1-methyl-2-oxo-3-quinolinecarboxamide in the batch using a suitable apparatus; and
    c) preparing the pharmaceutical composition from the batch only if the batch is determined to have less than about 0.50% N-ethyl-N-phenyl-1,2-dihydro-4,5-di-hydroxy-1-methyl-2-oxo-3-quinolinecarboxamide by weight relative to the amount of laquinimod.

In an embodiment of the process, in step c) the pharmaceutical composition is prepared from the batch only if the batch is determined to have less than about 0.10% N-ethyl-N-phenyl-1,2-dihydro-4,5-di-hydroxy-1-methyl-2-oxo-3-quinolinecarboxamide by weight relative to the amount of laquinimod.

In another embodiment of the process, in step c) the pharmaceutical composition is prepared from the batch only if the batch is determined to have less than about 0.05% N-ethyl-N-phenyl-1,2-dihydro-4,5-di-hydroxy-1-methyl-2-oxo-3-quinolinecarboxamide by weight relative to the amount of laquinimod.

In yet another embodiment of the process, in step c) the pharmaceutical composition is prepared from the batch only if the batch is determined to have less than about 0.02% N-ethyl-N-phenyl-1,2-dihydro-4,5-di-hydroxy-1-methyl-2-oxo-3-quinolinecarboxamide by weight relative to the amount of laquinimod.

The subject invention yet further provides a process for preparing a packaged pharmaceutical composition comprising laquinimod sodium comprising:
    a) obtaining a pharmaceutical composition of laquinimod or a pharmaceutically acceptable salt thereof;
    b) analyzing the pharmaceutical composition for the presence of N-ethyl-N-phenyl-1,2-dihydro-4,5-di-hydroxy-1-methyl-2-oxo-3-quinolinecarboxamide; and
    c) packaging the pharmaceutical composition in a light-resistant packaging only if the content of N-ethyl-N-phenyl-1,2-dihydro-4,5-di-hydroxy-1-methyl-2-oxo-3-quinolinecarboxamide is less than about 0.50% by weight relative to the amount of laquinimod.

In an embodiment of the process, in step c) packaging the pharmaceutical composition in a light-resistant packaging only if the content of N-ethyl-N-phenyl-1,2-dihydro-4,5-di-hydroxy-1-methyl-2-oxo-3-quinolinecarboxamide is less than about 0.10% by weight relative to the amount of laquinimod.

In another embodiment of the process, in step c) packaging the pharmaceutical composition in a light-resistant packaging only if the content of N-ethyl-N-phenyl-1,2-dihydro-4,5-di-hydroxy-1-methyl-2-oxo-3-quinolinecarboxamide is less than about 0.05% by weight relative to the amount of laquinimod.

In yet another embodiment of the process, in step c) packaging the pharmaceutical composition in a light-resistant packaging only if the content of N-ethyl-N-phenyl-1,2-dihydro-4,5-di-hydroxy-1-methyl-2-oxo-3-quinolinecarboxamide is less than about 0.02% by weight relative to the amount of laquinimod.

In yet another embodiment of the process, the light-resistant packaging is a blister packaging. In one embodiment, the blister packaging is opaque.

In yet another embodiment, the light-resistant packaging is an opaque high density polyethylene (HPDE) container.

The subject invention yet further provides a process of distributing a validated batch of a pharmaceutical composition comprising laquinimod or a pharmaceutically acceptable salt thereof and at least one pharmaceutically acceptable carrier, comprising:
    a) obtaining a batch of the pharmaceutical composition;
    b) performing stability testing with a sample of the batch;
    c) determining the total amount of N-ethyl-N-phenyl-1,2-dihydro-4,5-di-hydroxy-1-methyl-2-oxo-3-quinolinecarboxamide in the sample of the batch by a suitable apparatus after stability testing;
    d) validating the batch for distribution only if the sample of the batch after stability testing is determined to have less than about 0.50% by weight of N-ethyl-N-phenyl-1,2-dihydro-4,5-di-hydroxy-1-methyl-2-oxo-3-quinolinecarboxamide relative to the amount of laquinimod; and
    e) distributing the validated batch.

In an embodiment of the process, in step d) the batch is validated only if the sample of the batch after stability testing is determined to have N-ethyl-N-phenyl-1,2-dihydro-4,5-di-hydroxy-1-methyl-2-oxo-3-quinolinecarboxamide present in an amount of less than about 0.10% by weight relative to the amount of laquinimod.

In another embodiment of the process, in step d) the batch is validated only if the sample of the batch after stability testing is determined to have N-ethyl-N-phenyl-1,2-dihydro-4,5-di-hydroxy-1-methyl-2-oxo-3-quinolinecarboxamide present in an amount of less than about 0.05% by weight relative to the amount of laquinimod.

In yet another embodiment of the process, in step d) the batch is validated only if the sample of the batch after stability testing is determined to have N-ethyl-N-phenyl-1,2-dihydro-4,5-di-hydroxy-1-methyl-2-oxo-3-quinolinecarboxamide present in an amount of less than about 0.02% by weight relative to the amount of laquinimod.

In yet another embodiment of the process, the pharmaceutical composition comprises the pharmaceutically acceptable salt of laquinimod which is a sodium salt.

The subject invention yet further provides N-ethyl-N-phenyl-1,2-dihydro-4,5-di-hydroxy-1-methyl-2-oxo-3-quinolinecarboxamide or a salt thereof for use, as a reference standard to detect trace amounts of N-ethyl-N-phenyl-1,2-dihydro-4,5-di-hydroxy-1-methyl-2-oxo-3-quinolinecarboxamide in a pharmaceutical composition comprising laquinimod or a pharmaceutically acceptable salt of laquinimod.

The subject invention yet further provides a method for treating Multiple Sclerosis in a patient comprising administering to the patient an amount of the pharmaceutical composition described herein effective to treat Multiple Sclerosis in the patient.

The subject invention further provides the pharmaceutical composition described herein for use in treating Multiple Sclerosis in a patient.

The subject invention yet further provides a sealed package containing a pharmaceutical composition comprising laquinimod or a pharmaceutically acceptable salt thereof and at least one pharmaceutically acceptable carrier, wherein the sealed package is light resistant packaging.

In one embodiment, the light-resistant packaging is an opaque ampule, an opaque bag, an opaque blister pack, an opaque bottle, an opaque can, an opaque carton, an opaque drum, an opaque jar, an opaque pouch or an opaque tube.

In an embodiment, the light-resistant packaging is an opaque blister pack. In another embodiment, the opaque blister pack comprises a blend of aluminum and aluminum-silver. In another embodiment, the opaque blister pack comprises a blend of aluminum and poly-chloro-trifluoro-ethylene. In another embodiment, the opaque blister pack comprises a blend of two or more of polyvinyl chloride, polyethylene, polycarbonate, polyvinylidene chloride and ethylene vinyl alcohol.

In an embodiment, the light-resistant packaging is an opaque high density polyethylene (HPDE) container. In one embodiment, the opaque high density polyethylene (HPDE) container is an opaque high density polyethylene (HPDE) bottle. In another embodiment, the opaque high density polyethylene (HPDE) bottle is an opaque high density polyethylene bottle capped with polypropylene child-resistant screw caps fitted with a silica desiccant insert. In another embodiment, the opaque high density polyethylene (HPDE) bottle is an opaque high density polyethylene bottle capped with polypropylene child-resistant screw caps with aluminum induction seal.

Any embodiment disclosed herein can be combined with any other embodiment of the subject invention.

By any range disclosed herein, it is meant that all hundredth, tenth and integer unit amounts within the range are specifically disclosed as part of the invention. Thus, for example, 0.01 mg to 50 mg means that 0.02, 0.03 . . . 0.09; 0.1, 0.2 . . . 0.9; and 1, 2 . . . 49 mg unit amounts are included as embodiments of this invention.

A characteristic of a compound refers to any quality that a compound exhibits, e.g., peaks or retention times, as determined by 1H nuclear magnetic spectroscopy, mass spectroscopy, infrared, ultraviolet or fluorescence spectrophotometry, gas chromatography, thin layer chromatography, high performance liquid chromatography (HPLC), elemental analysis, Ames test, dissolution, stability and any other quality that can be determined by an analytical method. Once the characteristics of a compound are known, the information can be used to, for example, screen or test for the presence of the compound in a sample. Quantity or weight percentage of a compound present in a sample can be determined by a suitable apparatus, for example, a HPLC.

A "detection limit" for an analytical method used in screening or testing for the presence of a compound in a sample is a threshold under which the compound in a sample cannot be detected by the analytical method used. For example, the detection limit of a currently commercial HPLC method for 5-HLAQ in a sample containing laquinimod is 0.02% by weight relative to the amount of laquinimod.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^{1}H$, $^{2}H$, or $^{3}H$. Furthermore, any compounds containing $^{2}H$ or $^{3}H$ may specifically have the structure of any of the compounds disclosed herein.

Isotopically-labeled compounds can generally be prepared by conventional techniques known to those skilled in the art or by processes analogous to those described in the Examples disclosed herein using an appropriate isotopically-labeled reagents in place of the non-labeled reagents employed.

As used herein, a "low-light environment" is an environment substantially devoid of the presence of light having a wavelength of 310-400 nm. One example of a low-light environment is an environment enclosed with non-transparent vessels. Another example of a low-light environment is an environment in which yellow fluorescent light is used in place of standard fluorescent light. Yellow fluorescent light bulbs have filters which substantially limit the amount of light in the 310-400 nm wavelength range.

As used herein, a "light-resistant" packaging or coating is packaging or coating which inhibits the penetration of light, in particular fluorescent light, more particularly light having a wavelength of 310-400 nm.

As used herein, a "pharmaceutically acceptable" carrier or excipient is one that is suitable for use with humans and/or animals without undue adverse side effects (such as toxicity, irritation, and allergic response) commensurate with a reasonable benefit/risk ratio.

As used herein, "drug substance" refers to the active ingredient in a drug product, which provides pharmacological activity or other direct effect in the diagnosis, cure, mitigation, treatment, or prevention of disease, or to affect the structure or any function of the body of man or animals.

As used herein, "drug product" refers to the finished dosage form containing the drug substance as well as at least one pharmaceutically acceptable carrier.

As used herein, an "isolated" compound is a compound isolated from the crude reaction mixture following an affirmative act of isolation. The act of isolation necessarily involves separating the compound from the other known components of the crude reaction mixture, with some impurities, unknown side products and residual amounts of the other known components of the crude reaction mixture permitted to remain. Purification is an example of an affirmative act of isolation.

As used herein, a composition that is "free" of a chemical entity means that the composition contains, if at all, an amount of the chemical entity which cannot be avoided following an affirmative act intended to purify the composition by separating the chemical entity from the composition. A composition which is "free" of a laquinimod of a salt thereof, if present, as used herein, means that the laquinimod or a salt thereof is a minority component relative to the amount of 5-HLAQ, by weight.

As used herein, "stability testing" refers to tests conducted at specific time intervals and various environmental conditions (e.g., temperature and humidity) to see if and to what extent a drug product degrades over its designated shelf life time. The specific conditions and time of the tests are such that they accelerate the conditions the drug product is expected to encounter over its shelf life. For example, detailed requirements of stability testing for finished pharmaceuticals are codified in 21 C.F.R §211.166, the entire content of which is hereby incorporated by reference.

As used herein, "about" in the context of a measurable numerical value means the numerical value within the standard error of the analytical method used to measure.

A dosage unit may comprise a single compound or mixtures of compounds thereof. A dosage unit can be prepared for oral dosage forms, such as tablets, capsules, pills, powders, and granules.

Laquinimod and its salts can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit is preferably in a form suitable for oral administration. Laquinimod and its salts can be administered alone but is generally mixed with a pharmaceutically acceptable carrier, and co-administered in the form of a tablet or capsule, liposome, or as an agglomerated powder. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, dicalcium phosphate, calcium sulfate, mannitol, sorbitol, and the like. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators include, without limitation, starch, methyl cellulose, agar, bentonite, xanthan gum, croscarmellose sodium, sodium starch glycolate and the like.

Specific examples of the techniques, pharmaceutically acceptable carriers and excipients that may be used to formulate oral dosage forms of the present invention are described, e.g., in U.S. Patent Application Publication No. 2005/0192315, PCT International Application Publication Nos. WO 2005/074899, WO 2007/047863, and WO 2007/146248, the contents of which are incorporated herein by reference.

General techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol. 40 (Gilbert S. Banker, Christopher T. Rhodes, Eds.). These references in their entireties are hereby incorporated by reference into this application.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1

Formation of 5-HLAQ in Light Exposure of Laquinimod Solution

Various forms of laquinimod were exposed to light, as specified below. Presence of 5-HLAQ was determined using HPLC.

TABLE 1

| Light Source | Laquinimod medium | Presence of 5-HLAQ* (wt %) |
| --- | --- | --- |
| Light chamber 310-400 nm (~8 hrs.) | 1 mg/ml in 0.02M NaOH | 33 |
| Light chamber 310-400 nm (~8 hrs.) | 0.05 mg/ml in 0.02M NaOH | 71 |
| Light chamber 310-400 nm (~8 hrs.) | 0.05 mg/ml in 0.02M HCl | 1.5 |
| Sunlight cabinet (5 minutes) | 0.09 mg/ml aqueous solution | 11.8 |
| Sunlight cabinet (5 minutes) | Wet granulate** 0.2 mg/ml | 17.2 |
| Sunlight cabinet (20 minutes) | Milled granulate*** | 2.6 |

*The wt % of 5-HLAQ is a weight percent relative to laquinimod amount before applying photodegradation.
**Wet granulate was prepared by 1) mixing 90% of the total desired meglumine and mannitol in a high shear granulating mixer for 30 seconds, 2) mixing 10% of the total desired meglumine, a solution of laquinimod sodium, and purified water in a mixer until dissolved, and 3) adding the solution from 2) to the contents of the high shear granulating mixer and mixed.
***Milled granulate was prepared by drying the wet granulate in a fluid bed dryer at an inlet temperature of 50° C., then milling the dried granulate, which comprises of laquinimod sodium, meglumine and mannitol, using a 0.8 mm screen, and blending with sodium stearyl fumarate.

Discussion:

The results in Table 1 show that exposure to light sources, including florescent light or sunlight, can cause the transformation of laquinimod sodium, whether in solution, in solid powder form or granulate form, into 5-HLAQ. Solutions, both aqueous and non-aqueous, of laquinimod sodium are more susceptible to this transformation than solid forms.

Therefore, when preparing laquinimod compositions one or more of the steps listed below are contemplated to avoid formation of 5-HLAQ:

1. Combining laquinimod or salts thereof with water or other solvents in an environment free of light or in a low-light environment.
2. Admixing solutions of laquinimod or salts thereof with a pharmaceutically acceptable excipient in an environment free of light or in a low-light environment.
3. Manufacturing of laquinimod drug product using "yellow light" instead of standard lighting in an environment free of light or in a low-light environment.
4. Limiting exposure of solutions comprising laquinimod or salts thereof to fluorescent light while manufacturing laquinimod drug product.
5. Limiting exposure to light of laquinimod acid while being converted to a salt of laquinimod including laquinimod sodium.
6. Coating pharmaceutical formulations with a coating which inhibits light penetration. Colored coatings or coating containing Titanium Dioxide could be used as well, if they prevent penetration of light.

Example 2

Synthesis and Purification of N-ethyl-4,5-dihydroxy-1-methyl-2-oxo-N-phenyl-1,2-dihydroquinoline-3-carboxamide

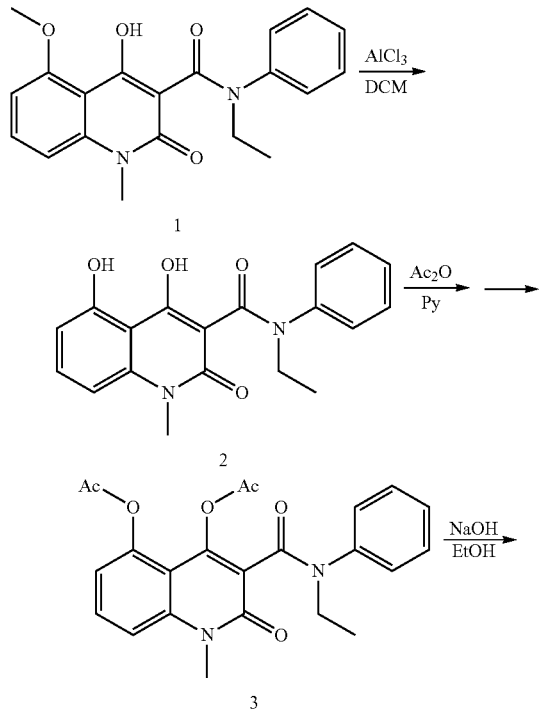

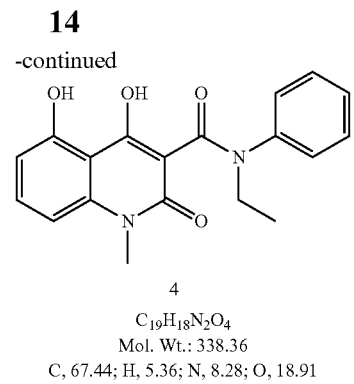

4

$C_{19}H_{18}N_2O_4$
Mol. Wt.: 338.36
C, 67.44; H, 5.36; N, 8.28; O, 18.91

5-MeO-LAQ (N-ethyl-4-hydroxy-5-methoxy-1-methyl-2-oxo-N-phenyl-1,2-dihydroquinoline-3-carboxamide, Compound 1) was prepared according to Journal of Medicinal Chemistry (2004), 47(8), 2075-2088.

Compound 1 (12.0 g, 0.034 mol) was dissolved in dichloromethane (DCM, 240 ml) and cooled at 0-5° C. AlCl$_3$ (12.0 g) was added and the reaction mixture was stirred for 0.5 hr at 0-5° C. followed by 7 hr at RT. The solution was evaporated to dryness at 30° C. (water bath) and water (300 ml) was added. The obtained grey solid was filtered, washed with 1N HCl (100 ml) and dried at 30° C. in vac oven. Yield: 14.5 g of Compound 2 (crude title compound).

Compounds, which have the same chemical structures as Compound 1 except for the substituent at position 5 of the dihydroquinoline ring, can also be used to prepare 5-HLAQ under suitable conditions. Such compounds can be prepared according to Journal of Medicinal Chemistry (2004), 47(8), 2075-2088.

Acetylation of Crude Title Compound:

Acetic anhydride (40 ml) was added to a solution of the crude title compound from the previous step (14.5 g) in Pyridine (100 ml) and the reaction mixture was stirred for 1 hr at room temperature. Pyridine was evaporated to dryness and the residue oil was dissolved in DCM (300 ml). The organic solution was washed with 1N HCl (200 ml) followed by water (200 ml×2). Crude Compound 3 (3-(ethyl(phenyl)carbamoyl)-1-methyl-2-oxo-1,2-dihydroquinoline-4,5-diyl diacetate) (15.5 g) was purified by flash chromatography on silica gel using a mobile phase of 1% MeOH in DCM. Yield: 10.2 g of Compound 3 (71% yield for two steps).

Hydrolysis of Compound 3 and Purification to Form Purified Title Compound:

1N NaOH solution (190 ml) was added to 5.6 g (0.013 mol) of Compound 3 suspended in EtOH (130 ml). The reaction mixture was stirred for 40 min and EtOH was evaporated (~150 ml). Residue was acidified with 5N HCl up to pH=1-2 and the white solid was filtered, washed with water and dried.

Yield: 4.3 g of N-Ethyl-N-phenyl-1,2-dihydro-4,5-di-hydroxy-1-methyl-2-oxo-3-quinolinecarboxamide, Compound 4 (98% yield, purity by HPLC >99%) as a white solid.

Identity and purity were verified by NMR, MS and EA.

Discussion:

N-Ethyl-N-phenyl-1,2-dihydro-4,5-di-hydroxy-1-methyl-2-oxo-3-quinolinecarboxamide (5-HLAQ) is not stable in most of the organic solvents as well as in aqueous acidic conditions. Therefore common purification methods were extremely difficult. The di-acetate derivative Compound 3 is an elegant way to purify the material followed only by basic hydrolysis, acidic precipitation and rapid filtration.

The synthesis enables the use of 5-HLAQ as a standard for the quantification of 5-HLAQ in a sample comprising a 5-HLAQ and laquinimod.

Example 3

Manufacture of Formulations Comprising Laquinimod Sodium

Capsules corresponding to 0.3 mg laquinimod acid per capsule (0.32 mg laquinimod sodium, 151.08 mg mannitol USP, 5.0 mg meglumine USP, 1.6 mg sodium stearyl fumarate NF) and 0.6 mg of laquinimod acid per capsule (0.64 mg laquinimod sodium, 302.16 mg mannitol USP, 10.0 mg meglumine USP, 3.2 mg sodium stearyl fumarate NF) were manufactured according to procedures described below:
1. Mixing 90% of the total desired meglumine and mannitol in a high shear granulating mixer for 30 seconds in a room in which the only source of light was yellow fluorescent lamp.
2. In a room in which the only source of light was yellow fluorescent lamp, mix 10% of the total desired meglumine, a solution of laquinimod sodium, and purified water in a mixer until dissolved.
3. In a room in which the only source of light was yellow fluorescent lamp, add the solution from step 2 to the contents of the high shear granulating mixer of step 1 to form a suitable granulate.
4. In a room in which the only source of light was yellow fluorescent lamp, dry the granulate in a fluid bed dryer with the inlet and outlet air temperatures of 50° C. and 40° C., respectively.
5. In a room in which the only source of light was yellow fluorescent lamp, mill the dry granulate using a 0.8 mm screen, and blend it with sodium stearyl fumarate.
6. In an enclosed environment with no light, fill the mixture from step 5 into size 3 hard gelatin capsules (0.3 mL volume) for the 0.3 mg of laquinimod acid dose and into size 1 hard gelatin capsules (0.5 mL volume) for the 0.6 mg laquinimod acid dose.

Discussion:

Example 3 demonstrated that in a commercial-scale production of laquinimod Drug Substances with non-detectable level of 5-HLAQ can be prepared in a low-light environment.

Example 4

Manufacture of Laquinimod Sodium Drug Substance

Four batches of laquinimod sodium drug substance were manufactured. The specification for impurities content for these batches was not more than (NMT) 1.0% of total impurities and less than (LT) 0.05% for any single impurity. During analysis, insufficient light protection of sample solution was provided. As a result, 5-HLAQ content of three of the four batches measured exceeded the specification (the 5-HLAQ contents were 0.04%, 0.11%, 0.06% and 0.05%).

Twelve additional batches of laquinimod sodium drug substance were manufactured at various manufacturing facilities. During analysis, sufficient light protection of sample solution was provided. The specification for 5-HLAQ content for these batches was NMT 0.1%. All twelve batches met the specification (one batch has 5-HLAQ content of less than 0.05, the remaining batch have 5-HLAQ content of less than 0.02, i.e., below detection limit).

Example 5

Manufacture of Laquinimod Sodium Drug Product

Twenty-six batches of laquinimod sodium drug product of various strengths were manufactured at various manufacturing facilities. Table 2 below shows the 5-HLAQ content for each batch.

TABLE 2

| Batch No. | Drug Product | 5-HLAQ Content (%) Specification NMT 0.5 |
|---|---|---|
| 1 | Laquinimod 0.6 mg capsules | <0.02* |
| 2 | Laquinimod 0.6 mg capsules | <0.02* |
| 3 | Laquinimod 0.6 mg capsules | <0.02* |
| 4 | Laquinimod 0.6 mg capsules | <0.02* |
| 5 | Laquinimod 0.6 mg capsules | <0.02* |
| 6 | Laquinimod 0.6 mg capsules | <0.02* |
| 7 | Laquinimod 0.6 mg capsules | <0.02* |
| 8 | Laquinimod 0.6 mg capsules | <0.02* |
| 9 | Laquinimod 0.6 mg capsules | <0.02* |
| 10 | Laquinimod 0.6 mg capsules | <0.02* |
| 11 | Laquinimod 0.6 mg capsules | <0.02* |
| 12 | Laquinimod 0.6 mg capsules | <0.02* |
| 13 | Laquinimod 0.6 mg capsules | <0.02* |
| 14 | Laquinimod 0.6 mg capsules | <0.02* |
| 15 | Laquinimod 0.6 mg capsules | <0.02* |
| 16 | Laquinimod 0.6 mg capsules | <0.02* |
| 16 | Laquinimod 0.3 mg capsules | <0.02* |
| 17 | Laquinimod 0.3 mg capsules | <0.02* |
| 18 | Laquinimod 0.3 mg capsules | <0.02* |
| 19 | Laquinimod 0.3 mg capsules | <0.02* |
| 20 | Laquinimod 0.3 mg capsules | 0.1* |
| 21 | Laquinimod 0.05 mg tablets | <0.1** |
| 22 | Laquinimod 0.25 mg tablets | <0.1** |
| 23 | Laquinimod 0.3 mg tablets | <0.03** |
| 24 | Laquinimod 0.3 mg tablets | <0.030** |
| 25 | Laquinimod 0.3 mg tablets | <0.030** |
| 26 | Laquinimod 0.3 mg tablets | <0.030** |

*Specification NMT 0.5
**Specification NMT 0.1

Discussion for Examples 4 and 5

Examples 4 and 5 demonstrate that batches of laquinimod drug substance and laquinimod drug product can be consistently produced meeting the specification for 5-HLAQ content.

Example 6

Laquinimod 0.6 mg White Opaque Capsules, Photo-Degradation Study

The goal of this study was to examine the photo-degradation of laquinimod 0.6 mg white opaque capsules after exposure to artificial sunlight in a glass plate (Petri dish) as compared to a glass plate covered by aluminum foil.

Materials and Methods

White opaque capsule shells were filled with laquinimod sodium 0.6 mg, and placed into photostability chamber in two Petri dishes, one plate open and one covered by aluminum foil.

The capsules were exposed to the following conditions:
1. Cool White Fluorescent Lamp, 11 days at 25° C./60% RH.
2. Near UV Fluorescent Lamp, 5 days at 25° C./60% RH.

Results

Exposure to artificial sunlight did not affect the appearance of capsules' body and content. Main Degradation products of laquinimod in the non-polar HPLC system appear at RRT 1.41 in the open plate only.

The results of testing in Polar HPLC system is shown in Table 3 below:

TABLE 3

|  | Dissolution % | Assay % | Degradation Products detected in Polar System, by Area % | |
|---|---|---|---|---|
|  |  |  | 5-HLAQ | Total |
| Time Zero | 99 | 99.6 | <0.03 | <0.05 |
| Aluminum Foil Covered Plate | 98 | 101.0 | <0.03 | <0.05 |
| Open Plate | 74 | 76.0 | 2.1 | 16.0 |

Conclusions & Results

Based on the results shown in Table 3 it can be concluded that laquinimod 0.6 mg white opaque capsules exposed to artificial sunlight are sensitive to light and the protection of the drug product provided by white opaque gelatin capsules is not enough.

Example 7

Laquinimod 0.6 Mg Capsules—Influence of Blister Pack Material on Photo-Degradation The goal of this study is to examine the photo-degradation of laquinimod sodium capsules, 0.6 mg, packed in blisters of various materials.

Materials and Methods

One batch of laquinimod sodium capsules, 0.6 mg/capsule was packed into four different types of blisters: PVC/AC/PVDC/PVLE/P058 504 142 (transparent), PVC/PE-EVOH/AC (A 300) G03 140 MM (transparent), A-/PVC/PE-EVOH/AC-PC (opaque), and KPMAX WH (opaque). Control was the same batch not exposed to sunlight in HDPE 50 cc DUMA™ bottle.

Results

The results are shown in Table 4.

Exposure to sunlight affected the appearance of capsules of laquinimod in clear blister packages, as well as the appearance of granulate.

No developing degradation products were detected in the Non-Polar HPLC system. However, they do appear in the Polar HPLC system.

TABLE 4

| Packaging Material | Appearance of Blister Package | Appearance of Granulate | Assay | 5-HLAQ |
|---|---|---|---|---|
| PVC/AC/PVDC/PVLE/P058 504 142 (transparent) | Intensively colored in brownish-gold | Yellowish powder | 53.0% | 1.8% |
| PVC/PE-EVOH/AC (A 300) G03 140 MM (transparent) | Colored in brownish-gold | Intensive yellowish powder | 38.6$ | 2.5% |
| A-/PVC/PE-EVOH/AC-PC (opaque) | Unchanged | White Powder | 94.7% | 0.28% |
| KPMAX WH (opaque) | Unchanged | White Powder | 99.1% | 0.07% |
| Control | N/A | White Powder | 98.3% |  |

Conclusions & Results

Laquinimod is sensitive to light. Opaque blisters, as compared to transparent, provide better protection of laquinimod from light against its photodegradation.

Example 8

Photostability of Laquinimod 0.6 mg Capsules in Various Packaging

Summary

The studies summarized in this section evaluated the stability of laquinimod 0.6 mg capsules after exposure to light outside the immediate pack and when packed in several immediate packaging configurations. The study results demonstrate that laquinimod 0.6 mg capsules drug product is unstable when directly exposed to light outside the immediate pack. By contrast, when the laquinimod 0.6 mg capsules drug product is packed in the immediate container closure systems being tested (three types of HDPE bottles with child resistance caps and aluminum/aluminum blisters) it is photostable when directly exposed to light. The photostability study was performed and all analytical parameters for all the tested packaging configurations were well within the rug product specification limits. It can be concluded that the three types of HDPE bottles with child resistance caps, and aluminum/aluminum blisters can be considered appropriate and suitable container closure systems for protecting laquinimod 0.6 mg capsules from light.

Procedure

In each of the two photostability studies performed, each tested packaging configuration was either directly exposed to artificial sunlight or wrapped in aluminum foil as a "dark control" to eliminate the possible effect of heating action of light. The tested container closure systems were exposed to cool white fluorescent light (approximately 5 KLUX) for 11 days (264 hours) followed by exposure to near ultraviolet (UV) light for additional 5 days (120 hours). Exposure limits are shown in Table 5 below:

TABLE 5

| Light Source | Minimal Exposure Limits | Time of Exposure |
|---|---|---|
| Cool White Fluorescent Lamp | 1.2 million lux hours | 11 days |
| New UV Fluorescent Lamp | 200 watt hours/square meter | 5 days |

The entire photostability study was carried out at 25° C. and at 60% relative humidity (RH) conditions. All samples described above were exposed to the Cool White Fluorescent Lamp (light capacity about 5 Klux/h) for 11 days under monitoring of exposure by using calibrated lux meter. Then all samples together with the quinine actinometric solution in quartz 1 cm UV cells (two cells not wrapped with aluminum foil and two cells wrapped with aluminum foil used as controls) placed on each shelf of the Climated Stability chamber were exposed to the Near UV Fluorescent Lamp for 5 days. After that, the absorbance of the actinometric solution and its wrapped control solution on each shelf was measured at 400 nm to ensure a change in absorbance of not less than 0.5 between the non-wrapped actinometric solution and its wrapped control on each shelf.

For this purpose the actinometric solutions (wrapped and not wrapped) were removed from the stability chamber, transferred in light resistance containers to the analytical laboratory and submitted for UV testing. Each sample type along with its control was tested for assay, dissolution, impurities, water content and appearance.

Study 1

The first study tested whether the drug product is photostable when exposed to light outside its immediate pack. The photostability of capsules packed in transparent and opaque blisters was also tested as follows:
1. Unpacked capsules in a closed transparent Quartz dish. The capsules were inserted into the Quartz dish to form one layer of capsules in a way that they do not touch each other.
2. Transparent Aluminum/Aclar® (KPMAX®) blister packs containing 10 capsules per card.
3. White opaque Aluminum/Aclar® (KPMAX®) blister packs containing 10 capsules per card.

Study 2

The second photostability study tested the protection from light of laquinimod 0.6 mg capsules packed in various immediate container closure system:

Container System 1:
White 50 cc round opaque high density polyethylene containers (DUMA™ system) capped with white round polypropylene child-resistant screw caps fitted with a silica desiccant insert. The bottle is filled with 30 capsules and contains cotton wool located between the capsules and the cap.

Container System 2:
White 100 cc round opaque high density polyethylene containers (DUMA™ system) capped with white round polypropylene child-resistant screw caps fitted with a silica desiccant insert. The bottle is filled with 90 capsules and contains cotton wool located between the capsules and the cap.

Container System 3:
White 60 cc round opaque high density polyethylene containers capped with white round polypropylene child-resistant screw caps with aluminum induction seal. The bottle is filled with 30 capsules and also contains a silica desiccant canister and cotton wool located between the capsules and the cap.

Container System 4:
Aluminum-silver/aluminum-soft blister packs containing 7 capsules per card.

Conclusions & Results

The results of studies 1 and 2 are summarized in Table 6 below:

TABLE 6

| Config-<br>uration | Interval | Assay<br>Specifi-<br>cation:<br>95.0-105.0% | 5-HLAQ<br>Content<br>Specifi-<br>cation:<br>NMT 0.5% | Total polar<br>IDD**<br>Specifi-<br>cation:<br>NMT 2.0% |
|---|---|---|---|---|
| Unpacked | Time zero | 96.8 | <0.02 | <0.05 |
| capsules | Covered* | 99.7 | <0.02 | 0.06 |
| (Quartz dish) | Not covered* | 78.7 | 1.6 | 11.8 |
| Transparent | Time zero | 99.0 | <0.02 | <0.05 |
| KPMA | Covered* | 98.8 | <0.02 | <0.05 |
|  | Not covered* | 76.7 | 2.3 | 13.1 |
| Opaque | Time zero | 101.1 | <0.02 | <0.05 |
| KPMAX | Covered* | 98.6 | <0.02 | <0.05 |
|  | Not covered* | 98.9 | <0.02 | <0.05 |
| Container | Time zero | 99.0 | <0.02 | <0.05 |
| System 1 | Covered* | 98.8 | <0.02 | <0.05 |
|  | Not covered* | 99.8 | <0.02 | <0.05 |
| Container | Time zero | 99.9 | <0.02 | <0.05 |
| System 2 | Covered* | 100.1 | <0.02 | <0.05 |
|  | Not covered* | 99.7 | <0.02 | <0.05 |
| Container | Time zero | 100.0 | <0.02 | <0.05 |
| System 3 | Covered* | 99.9 | <0.02 | <0.05 |
|  | Not covered* | 100.2 | <0.02 | <0.05 |
| Container | Time zero | 100.5 | <0.02 | <0.05 |
| System 4 | Covered* | 99.0 | <0.02 | <0.05 |
|  | Not covered* | 100.1 | <0.02 | <0.05 |

*Covered or not covered with aluminum foil and exposed to a Cool White Fluorescent Lamp for 11 days followed by exposure to Near UV Fluorescent Lamp for 5 days.
**Impurities/Degradation Products Determination An out of specification (OOS) assay result of 78.1 was observed for the unpacked capsules when exposed to light. In addition, the 5-HLAQ polar impurity levels observed were OOS and the total polar impurities level was 11.8%. The exposure of the transparent KPMAX blisters to light gave very similar results as those of the unpacked capsules. By contrast, the results of the dark control samples (Quartz dish wrapped with aluminum and transparent KPMAX blisters wrapped with aluminum) that were not exposed to light were acceptable and well within the speciation results. In addition, the white opaque KPMAX blisters (both control and samples directly exposed to light) gave satisfactory results that are well within the drug product specifications.

The results of Study 1 demonstrate that the drug product outside its immediate pack is not phtostable and protection from light should be considered when choosing an appropriate container closure system. In study 2 no significant difference in assay dissolution, water content, appearance, impurities formation and photostability was observed between the different packaging configurations when exposed to light. In addition, there is no difference in photostability results between time zero and end of photostability intervals, and between the exposed and dark control results for all immediate configurations tested.

What is claimed is:

1. A pharmaceutical composition comprising laquinimod or a pharmaceutically acceptable salt thereof, and 1) N-ethyl-N-phenyl-1,2-dihydro-4,5-di-hydroxy-1-methyl-2-oxo-3-quinolinecarboxamide or a salt thereof, wherein N-ethyl-N-phenyl-1,2-dihydro-4,5-di-hydroxy-1-methyl-2-oxo-3-quinolinecarboxamide is present in the composition in an amount greater than about 0.02% and less than about 0.50%, by weight, relative to the amount of laquinimod, based on a determination by an HPLC method; or 2) at least one pharmaceutically acceptable carrier, and a light-resistant coating wherein the coating is resistant to light with wavelength in the range of 310-400 nm.

2. The pharmaceutical composition of claim 1, wherein the amount of N-ethyl-N-phenyl-1,2-dihydro-4,5-di-hydroxy-1-methyl-2-oxo-3-quinolinecarboxamide in the composition is greater than about 0.02% and less than about 0.10% by weight relative to the amount of laquinimod.

3. The pharmaceutical composition of claim 1, wherein the amount of N-ethyl-N-phenyl-1,2-dihydro-4,5-di-hydroxy-1-methyl-2-oxo-3-quinolinecarboxamide in the composition is greater than about 0.02% and less than about 0.05% by weight relative to the amount of laquinimod.

4. A process for preparing a pharmaceutical composition comprising laquinimod or a pharmaceutically acceptable salt thereof, comprising: admixing laquinimod or a pharmaceutically acceptable salt thereof with at least one pharmaceutically acceptable carrier in a low-light environment to form the pharmaceutical composition, wherein the pharmaceutical composition further comprises N-ethyl-N-phenyl-1,2-dihydro-4,5-di-hydroxy-1-methyl-2-oxo-3-quinolinecarboxamide in an amount of less than 0.5% by weight relative to the amount of laquinimod.

5. A process for preparing a validated pharmaceutical composition comprising laquinimod or a pharmaceutically acceptable salt thereof, and at least one pharmaceutically acceptable carrier, comprising:
   a) obtaining a batch of laquinimod or a pharmaceutically acceptable salt thereof;
   b) determining the amount of N-ethyl-N-phenyl-1,2-dihydro-4,5-di-hydroxy-1-methyl-2-oxo-3-quinolinecarboxamide in the batch using a suitable apparatus; and
   c) preparing the pharmaceutical composition from the batch only if the batch is determined to have less than about 0.50% N-ethyl-N-phenyl-1,2-dihydro-4,5-di-hydroxy-1-methyl-2-oxo-3-quinolinecarboxamide by weight relative to the amount of laquinimod.

6. The process of claim 5, wherein in step c) the pharmaceutical composition is prepared from the batch only if the batch is determined to have less than about 0.02% N-ethyl-N-phenyl-1,2-dihydro-4,5-di-hydroxy-1-methyl-2-oxo-3-quinolinecarboxamide by weight relative to the amount of laquinimod.

7. A process for preparing a packaged pharmaceutical composition comprising laquinimod or a pharmaceutically acceptable salt thereof comprising:
   a) obtaining a pharmaceutical composition of laquinimod or a pharmaceutically acceptable salt thereof;
   b) analyzing the pharmaceutical composition for the presence of N-ethyl-N-phenyl-1,2-dihydro-4,5-di-hydroxy-1-methyl-2-oxo-3-quinolinecarboxamide; and
   c) packaging the pharmaceutical composition in a light-resistant packaging only if the content of N-ethyl-N-phenyl-1,2-dihydro-4,5-di-hydroxy-1-methyl-2-oxo-3-quinolinecarboxamide is less than about 0.50% by weight relative to the amount of laquinimod.

8. The process of claim 7, wherein in step c) packaging the pharmaceutical composition in a light-resistant packaging only if the content of N-ethyl-N-phenyl-1,2-dihydro-4,5-di-hydroxy-1-methyl-2-oxo-3-quinolinecarboxamide is less than about 0.02% by weight relative to the amount of laquinimod.

9. A process of distributing a validated batch of a pharmaceutical composition comprising laquinimod or a pharmaceutically acceptable salt thereof and at least one pharmaceutically acceptable carrier, comprising:
   a) obtaining a batch of the pharmaceutical composition;
   b) performing stability testing with a sample of the batch;
   c) determining the total amount of N-ethyl-N-phenyl-1,2-dihydro-4,5-di-hydroxy-1-methyl-2-oxo-3-quinolinecarboxamide in the sample of the batch by a suitable apparatus after stability testing;
   d) validating the batch for distribution only if the sample of the batch after stability testing is determined to have less than about 0.50% by weight of N-ethyl-N-phenyl-1,2-dihydro-4,5-di-hydroxy-1-methyl-2-oxo-3-quinolinecarboxamide relative to the amount of laquinimod; and
   e) distributing the validated batch.

10. The process of claim 9, wherein in step d) the batch is validated only if the sample of the batch after stability testing is determined to have N-ethyl-N-phenyl-1,2-dihydro-4,5-di-hydroxy-1-methyl-2-oxo-3-quinolinecarboxamide present in an amount of less than about 0.02% by weight relative to the amount of laquinimod.

11. The pharmaceutical composition of claim 1, comprising the pharmaceutically acceptable salt of laquinimod which is a sodium salt.

12. The pharmaceutical composition of claim 1, further comprising at least one pharmaceutically acceptable carrier.

13. The pharmaceutical composition of claim 12, wherein the at least one pharmaceutically acceptable carrier is magnesium stearate.

14. The pharmaceutical composition of claim 1, in the form of a capsule or a tablet.

15. The pharmaceutical composition of claim 14, wherein the pharmaceutical composition is a tablet coated with a light-resistant coating, and/or is in light-resistant packaging.

16. The pharmaceutical composition of claim 15, wherein 1) the light-resistant coating is a coating comprising titanium dioxide, and/or 2) the light-resistant packaging is an opaque blister pack or an opaque high density polyethylene (HPDE) container.

17. The pharmaceutical composition of claim 1, which is a solid pharmaceutical composition.

* * * * *